United States Patent [19]

Asano et al.

[11] Patent Number: 4,708,882

[45] Date of Patent: Nov. 24, 1987

[54] METHOD FOR DETECTING FINGERPRINTS USING A LASER AND AN APPARATUS THEREFOR

[75] Inventors: Yuichiro Asano; Yoshihisa Kono; Takayuki Yanagimoto; Motoji Shiozumi; Kunio Takahashi; Akira Torao, all of Chiba; Susumu Moriya; Atsushi Momose, both of Hyogo, all of Japan

[73] Assignee: Kawasaki Steel Corporation, Hyogo, Japan

[21] Appl. No.: 810,988

[22] Filed: Dec. 19, 1985

[30] Foreign Application Priority Data

Dec. 27, 1984 [JP] Japan ................................ 59-280888
Dec. 27, 1984 [JP] Japan ................................ 59-280889
Apr. 17, 1985 [JP] Japan ................................ 60-82003

[51] Int. Cl.$^4$ .............................................. A61B 5/10
[52] U.S. Cl. ...................................... 427/1; 427/145; 427/157; 427/430.1
[58] Field of Search ................. 427/1, 429, 53.1, 157, 427/353, 256, 145, 430.1

[56] References Cited

U.S. PATENT DOCUMENTS 4,226,740 10/1980 Worsham et al. .................. 427/145
4,303,701 12/1981 Torgensen et al. ................. 427/157

OTHER PUBLICATIONS

Menzel, Identification News, International Ass. for Identification, vol. XXXIII, No. 9, Sep. 1983, pp. 7 and 11.

Primary Examiner—Janyce A. Bell
Attorney, Agent, or Firm—Bierman & Muserlian

[57] ABSTRACT

In one aspect of the invention, the sample surface is wetted with an aqueous solution of a fluorescent dye followed by rinses with water to remove an excessive amount of the dye so that the background fluorescence emission can be minimized to increase the efficiency of fingerprint detection. In another aspect, the fluorescent dye or a reagent to produce fluorescent substance is deposited on the sample surface by attaching a gelatin film impregnated with a solution thereof followed by peeling. In a further different aspect, a powdery fluorescent dye is deposited on to the sample surface followed by spraying of water after removing an excessive amount of the powdery dye so that the background fluorescence can be minimized. The invention also provides an apparatus for the fingerprint detection by the laser beam excitation of fluorescence, which is compact and portable as being composed of an ingenious combination of several units into an integral system.

1 Claim, 7 Drawing Figures

METHOD FOR DETECTING FINGERPRINTS USING A LASER AND AN APPARATUS THEREFOR

BACKGROUND OF THE INVENTION

The present invention relates to a method for detecting fingerprints deposited on various substrate bodies using a laser and an apparatus therefor useful in the field of criminal identification.

As is known, various methods are used in the prior art for the detection of a latent fingerprint including the solid methods, in which a powder of aluminum and the like is sprinkled over the samples and deposited on the moisture and fat in the secretion deposited on the sample so as to produce visually detectable difference in the color tone between the background surface and the fingerprint pattern, liquid methods, in which the amino acids and salinity contained in the deposited secretion are subjected to a color reaction with a chemical reagent, and gas methods, in which the fat contained in the deposited secretion is reacted with iodine gas to cause coloration.

These prior art methods, however, are not free from several disadvantages and defects that the detecting power thereof is low when the fingerprint is aged after deposition on the sample or when the fingerprint is deposited on the surface of a certain kind of samples such as non-traditional building materials coated with a surface film of a polymer and that the sample is sometimes stained or contaminated unduly. As a remedy for these defects, an improved method has been proposed by utilizing the fluorescence produced by the irradiation with a laser beam in several publications including:

(1) E. R. Menzel, Identification News, International Association for Identification, volume XXXIII, No. 9 (September, 1983); and (2) R. D. Olsen, Identification News, International Association for Identification, volume XXXIV, No. 4 (April, 1984).

The so-called laser fluorescence methods hitherto reported are classified into three classes of:

(a) a method in which the fingerprint as deposited is irradiated as such with a laser beam and the fluorescence emitted from an ingredient, e.g. riboflavin, in the fingerprint is utilized for detection;

(b) a method in which certain constituents, e.g. amino acids, urea and the like, in the secretion are reacted with a chemical reagent to be converted into a fluorescent material before irradiation with a laser beam; and (c) a method in which the sample bearing a latent fingerprint deposited thereon is first contacted with a fluorescent dye before irradiation with a laser beam.

The above mentioned method (a) is, however, hardly applicable to a sample emitting a relatively strong background fluorescence to mask the generally weak fluorescence from the fingerprint pattern since a fingerprint usually contains only an extremely small amount of the fluorescence-emitting constituents other than water although the method is advantageous in respect of the absence of contamination on the surface of the sample.

The above mentioned methods (b) and (c) are more effective than the method (a) when the sample bearing the fingerprint emits a background fluorescence but these methods are not free some problems as given below in respect of the procedure of dipping the sample in the reagent solution or coating or spraying a solution of the reagent or dye on to the sample.

The above described prior art publications (1) and (2) describe a method of dipping the sample in the reagent solution or spraying the reagent solution to the sample, of which following disadvantages are unavoidable.

(i) When a sample bearing a latent fingerprint deposited thereon is dipped in a dye solution, it is usual that the solution adheres to the surface in a more than sufficient amount. Accordingly, the fluorescence may be emitted not only from the lines of the fingerprint pattern but also from the background surface almost as strongly as from the fingerprint lines per se so that difficulties are encountered in detecting and identifying the image of the fingerprint.

(ii) It is essential in practicing the method to strictly control the conditions of dipping or spraying. For example, the length of time for dipping in the case of the dipping procedure and the volume of sprayed solution in the case of spraying procedure must always be kept constant making the method very troublesome or time-consuming. when an excessively large volume of the reagent solution is taken up on the surface of the sample, in addition, the ingredients in the fingerprint secretion or reaction products thereof on the sample may sometimes be dissolved or eluted out in the solution so that distinctness of the fluorescent fingerprint image is decreased as a consequence.

(iii) The method is poorly versatile because the method is practiced using a solution of the reagent or dye in the actual spot of, for example, a criminal case. In addition, the sample is sometimes unduly contaminated with the solution. Further, the spraying procedure naturally requires a sprayer which is not always convenient in handling even by setting aside the disadvantage due to the cost therefor.

The method (c), which is advantageous in the presence of a relatively strong background emission, has problems of fluorescence emission from the dye extraneously deposited on the portions outside the fingerprint lines and indistinctness of the fingerprint lines due to the dissolution of the fingerprint secretion in the solvent of the dye solution. Further, the surface of the sample is unduly contaminated with the dye solution and this disadvantage is particularly serious when the sample is made of a material readily soaked with the solution such as paper or cloth.

The publication (1) for the method (c) describes particular examples using rhodamine 6G and ninhydrin as the typical dyes.

According to the disclosure for the procedure using rhodamine 6G, a methyl alcohol solution of the dye is applied or sprayed to the sample followed by drying and the sample is irradiated with the laser beam. It is taught here that an excessive amount of rhodamine 6G deposited on the surface should be removed by washing with methyl alcohol.

The applicablility of this method to practical cases is, however, questionable in respect of the detecting power of fingerprints due to the following difficulties. When methyl alcohol is used as the solvent, the wettability of the surface of samples is usually much larger to methyl alcohol than to water and the dye solution is dried up as such so that the dye is deposited and adheres in a considerably large amount to the surface outside the fingerprint lines to cause difficulties in distinguishing the fluorescence from the fingerprint lines alone. Methyl alcohol in itself is not suitable as the solvent used in this purpose because methyl alcohol has dissolving power of the fatty ingredients in the fingerprint secretion and dehydrating power to cause loss of a large part of the fingerprint ingredients. In addition, some of the materials forming the samples are susceptible to the attack of methyl alcohol. When an excessively deposited dye is removed by washing with methyl alcohol, the dye once fully dried and firmly adhering to the surface can hardly be washed away without the danger of losing a large part of the fingerprint ingredients.

An alternative method belonging to the method (c) utilizes a chemical reaction of ninhydrin typically applicable to the detecting purpose of fingerprints deposited on a sample readily soaked with a liquid.

In a practical procedure using ninhydrin, the sample is coated with ninhydrin followed by drying to produce a contrast in color between the background and the fingerprint deposition by which the fingerprint can be detected. A problem in this method is the inapplicability of the method to certain samples such as thermosensitive paper and the like because blackening takes place all over the areas coated with ninhydrin rendering detection of the fingerprint lines impossible.

Various types of apparatuses for the detection of fingerprints using a laser are commercially available as manufactured by American companies including (3) Spectra Physics Co., (4) Laser Ionics Co., (5) Plasma Kinetics Co. and (6) Laser Photonics Co. according to their catalogues.

A major current of the fingerprint detecting methods using a laser utilizes the principle according to which a fluorescent substance deposited on the fingerprint lines by a suitable method is excited by the irradiation with a laser beam to emit fluorescence detectable as a fingerprint image. The laser beam is usually green in color so that the a fluorescence emission is obtained in the longer wavelength region ranging from yellow to orange. The prior art technology in connection with the detecting instrument can be classified into two classes as described below.

(1) The instrument is constructed either of three parts including a laser unit composed of a laser oscillator and a power supply therefor, an image-receiving unit composed of a sharp-cut filter and a two-dimensional image receiver and an image monitoring unit or of the laser unit alone leaving the procedure of the fingerprint detection to visual inspection through an optical filter. The laser used here is a large argon ion laser or a copper vapor laser.

The laser unit in the instruments of this type is usually large and heavy and requires supply of cooling water and large electric current with poor portability and mobility as a serious disadvantage. Accordingly, most of the conventional instruments of this type must be installed in a station for the works of fingerprint detection and identification.

(2) On the other hand, the fingerprint detector instrument manufactured by Laser Photonics Co. is portable with a small YAG laser although the instrument is constructed with the units of the same type as in the instruments described in (1) above. In this instrument, the laser beam is conducted to the sample bearing a latent fingerprint by means of an optical fiber to excite the fluorescence emission from the fingerprint lines and the image of the fluorescent fingerprint is taken by a separate TV camera. Further, a super-high sensitivity image receiver is used as the two-dimensional image receiver in this instrument so that the image receiving unit cannot be compact with additional disadvantages in respect of the S/N ratio and resolution of the fingerprint images.

Though advantageous in respect of the absence of necessity of moving the laser oscillator, the instrument of this type is disadvantageous because the operability of the instrument is poor as a result of the separate installation of the units for the laser beam irradiation and image receiving. Moreover, the instrument cannot be operated by a single operator.

In addition, each of the above described instruments (1) and (2) cannot be a single integral unit because of the dimensions and weight of each of the component units to decrease the operability of the instrument. Further, there may be some danger when the diffused reflection of the laser beam from the sample hits the operator's eyes. This problem is particularly serious when the laser is a high output one.

SUMMARY OF THE INVENTION

An object of the present invention is to provide a method for obtaining a clear and distinct fluorescent image of a fingerprint using a laser with suppression of the emission from the background surface of a sample bearing the fingerprint.

Another object of the present invention is to provide a method for detecting a clear and distinct fingerprint image with stability conveniently and inexpensively by preventing adherence of an excessive amount of a reagent or dye to the fingerprint.

A further object of the invention is to provide a method for preventing the disadvantages in the prior art method using methyl alcohol as the solvent for a dye to destroy the fingerprint lines per se or to attack the surface of the sample by use of a water-soluble fluorescent dye and water as the solvent therefor and also a method for minimizing the amount of the dye deposited on the sample surface outside the fingerprint lines by rinsing the sample surface with water before complete drying of the dye solution adhering to the sample surface so as to wash away the dye precipitated in the solution before deposition thereof all over the surface of the sample.

A still further object of the invention is to provide a method by which fingerprints can be detected with high probability even on a sample which is not susceptible to the detection of a fingerprint by the conventional powder method such as a printed plywood and gravure paper or a sample readily soaked with liquids such as paper or cloth on which fingerprints cannot be detected by the method of chemical reaction.

A further important object of the invention is to provide an apparatus for the detection of fingerprints in a compactly integrated unit from with good mobility and operability and capable of giving high-quality fingerprint images.

Another object of the invention relative to the apparatus is to provide an apparatus for the detection of fingerprints suitable for the works of searching the surface spot of a sample bearing a fingerprint or detection of a fingerprint by visual inspection utilizing a laser beam not only in laboratories but also in the actual spot of criminal cases without any danger due to the diffused reflection of the laser beam hitting the eyes of the persons therearound.

The above described objects can well be achieved by the method of the present invention having the characteristic features described below.

In the method for the detection of a fingerprint utilizing fluorescene excited by the irradiation with light, namely, an aqueous solution of a water-soluble fluorescent dye is contacted to the sample, the sample is rinsed with clean water before the aqueous solution adhering to the surface of the sample is completely dried and then the surface of the sample is irradiated with light having a wavelength sufficient to excite the dye in the aqueous solution to emit fluorescence so that an image of the fingerprint lines is obtained by the fluorescence from the fingerprint.

Alternatively, a gelatin film(s) impregnated with a solution of a chemical reagent or dye dissolved therein is brought into contact with the surface of a sample bearing a fingerprint so as to have the surface fully wet with the solution followed by removing of the gelatin film(s) and irradiation of the surface with exciting light to give a fluorescent image.

When the method of the invention is practiced as a powder method, a fluorescent dye in a powdery form is deposited on the surface of a sample, water is sprayed to the surface of the sample after removing the excessive amount of the powdery dye deposited thereon and then the surface is irradiated with light having a wavelength sufficient to have the dye excited to emit fluorescence so that an image of the fingerprint pattern is obtained by the fluorescence from the fingerprint lines.

The inventive apparatus for the detection of fingerprints comprises a detecting head, a power source unit for laser, a unit for the processing of image memory and a control circuit unit for the synchronous control thereof or, alternatively, the apparatus comprises an optical fiber for transmission of light, an optical system which serves to expand the laser beam and irradiate the surface of a sample with the expanded laser beam and an image receiving unit formed by integrally combining a two-dimensional image pickup device and an optical system in a portable fashion.

Further, in the method for the detection of a latent fingerprint by the laser-induced fluorescence method, a laser beam generated by a laser oscillator is expanded by means of a lens system, the expanded laser beam is brought into intermittent scanning in a definite direction according to the intensity distribution of the laser beam, the detected image is written in the image memory with the laser beam scanning interrupted at several positions of the interrupted laser beam scanning and these image data are integrated to make the fingerprint image clearer and more distinct.

DETAILED DESCRIPTION OF THE PREFERRED EMBODIMENTS

Figure 1:
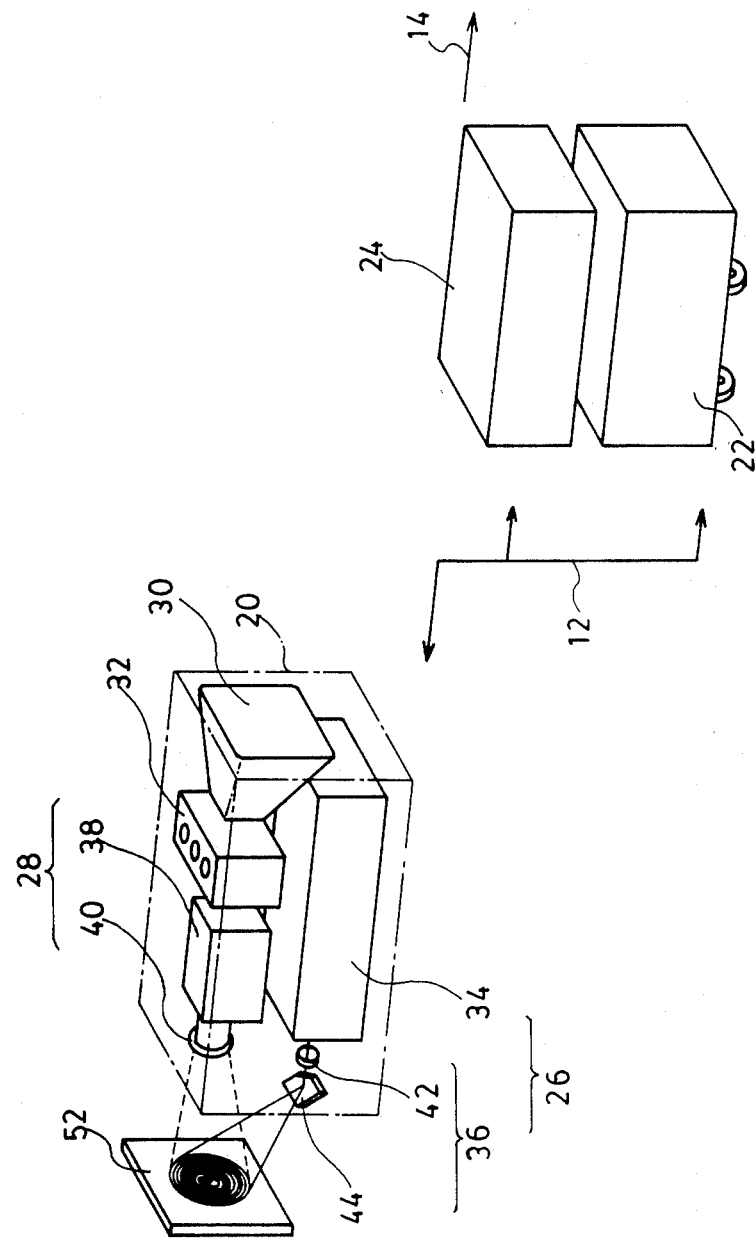
FIG. 1 is a perspective view of an inventive apparatus for the detection of fingerprints described in the first example.

In the following, the method and apparatus of the present invention are described in detail.

As a result of the extensive investigations, the inventors have achieved experimental recognition of the defects and disadvantages in the prior art methods for the detection of fingerprints using methyl alcohol and have discovered a method by which fingerprints can be detected with a very high probability by improving the defective points in the prior art.

The inventive method, which provides a solution for the above mentioned problems, essentially utilizes a watersoluble fluorescent dye as the dye and water as the solvent for the fluorescent dye and the surface of the sample is first wetted with an aqueous solution of the dye and then rinsed with clean water prior to complete drying followed by a known procedure including drying and irradiation with light such as a laser beam having a wavelength capable of exciting the dye to efficiently emit fluorescence.

The use of a water-soluble fluorescent dye as the dye and water as the solvent provides a means dissolving the difficulties in the prior art method using methyl alcohol such as the damage to the fingerprint lines per se and attack to the surface of the sample.

The rinse of the sample surface with water before complete drying of the dye solution on the sample surface has an effect to wash away the precipitated dye in the solution in the form of an aqueous solution before it is deposited on and adheres to the sample surface overall so that the amount of the dye deposited on the surface outside the fingerprint lines can be minimized. The rinse with water should be performed before complete drying of the dye solution on the surface which means that the aqueous solution remaining on the surface is saturated with the dye by the partial evaporation of water or absorption of water into the underlying sample surface. The sequence of the above described steps is effective to minimize the fluorescence emission from the background surface to give a clear and distinct fluorescent image of the fingerprint pattern.

By practicing the above described method for the detection of fingerprints, it is possible to detect a fingerprint with a very high probability even on certain samples, such as untraditional building materials, gravure paper and the like, to which the powder method in the prior art is hardly applicable. Water as the solvent of the dye is easy in handling and negligible in cost in comparison with methyl alcohol used in the prior art methods in addition to the greatly decreased contamination of the sample surface by the dye since the excessive portion of the dye on the surface has been almost completely washed away.

In the next place, description is given on the techniques applicable to a sample which can readily be soaked with liquids.

Gelatin film(s) in general are insoluble in a typical solvent of dyes such as methyl alcohol, ethyl alcohol, distilled water, acetone and the like but can be impregnated with a solution more or less. The method of the present invention utilizes a gelatin film(s) for the detection of a fingerprint and is performed in the following procedure.

(1) A gelatin film(s) used which is impregnated with a suitable volume of a solution of the chemical reagent or dye.

The chemical reagents usable in this case include the fluorescence reagents for amino acids such as 7-chloro-4-nitrobenzo-oxa-1,3-azole soluble in methyl alcohol and orthophthalic aldehyde soluble in water and the fluorescence reagents for urea such as p-dimethylaminocinnamaldehyde soluble in acetone and the fluorescent dyes include rhodamine 6G and coumarin each soluble in methyl alcohol. The gelatin film(s) is impregnated with 80 to 99% by weight of a solution of these reagents or dyes.

(2) A gelatin film(s) impregnated with a solution of the above named reagent or dye is brought into direct contact with the surface of a sample bearing a latent fingerprint and kept as such for a sufficient length of time to ensure the reaction between the reagent and the ingredients in the fingerprint secretion or dyeing of the fingerprint constituents with the dye.

The length of time for keeping the gelatin film(s) in contact with the sample surface should approximately be in the range from several tens of minutes to several days for chemical reagents and from several minutes to several tens of minutes for dyes though dependent on the kind of the chemical reagent, dye or solvent, temperature, age of the fingerprint from deposition and other conditions.

(3) After peeling of the gelatin film(s) off the surface of the sample, the surface is irradiated with light such as a laser beam capable of exciting the respective reaction product or the dye to emit fluorescence and the thus obtained image of flourescence is detected by means of the image pickup unit.

When the above described procedure is practiced, the fingerprint can be contacted always with a controlled amount of the chemical reagent or dye so that the difficult problems in the prior art methods for the detection of fingerprints can be dissolved such as excessively intense fluorescence emission from the portions outside the fingerprint lines due to the unduly large amount of deposition of the reagent or dye and loss of the fingerprint constituents or the reaction product by effluence.

Further, the works of fingerprint detection can be performed very conveniently according to the inventive method by using a gelatin film(s) prepared in advance and impregnated with a solution of the chemical reagent or dye in the actual spot where detection of a fingerprint is required. No difficulties are encountered of course in the transportation thereof. Furthermore, the system for the detection of fingerprint is outstandingly inexpensive because no sprayer and other machines are required.

Following is a description of the solution of the problems when the sample is readily soaked with a liquid. In this case, a yellow dye in a powdery form is used as the fluorescent dye. The yellow dye is sprinkled and deposited on the surface of the sample and, after removal of a excessive amount thereof from the surface, water is sprayed thereto followed by the irradiation of the surface with light such as a laser beam of a wavelength capable of efficiently exciting the powdery dye to emit fluorescence.

The above mentioned combination of the flourescent dye in the form of a dry powder as the dye and spraying of water thereto can provide a means for overcoming the disadvantages in the prior art methods such as destruction of the fingerprint lines per se and attack to the surface of the sample so that a clear and distinct fluorescent image can be obtained by this means.

By practicing the above described method, fingerprints can be detected with a very high probability even on certain samples, such as cloths, specialty papers and the like, for which the conventional powder method is powerless in the detection of a fingerprint aged after deposition.

Following is a description on the improvement of the apparatus for the detection of fingerprints using a laser beam.

Thus, the apparatus of the present invention for the detection of fingerprints comprises:

(1) a compact and highly portable detector head unit integrally composed of a laser beam projector, image receiver unit and picture monitor;

(2) a power source unit for the laser;

(3) an image memory processing unit for the addition or reduction memory processing of the picture image in the above mentioned image receiver unit; and (4) a control circuit unit which synchronously control the above mentioned detector head, power source unit for the laser and image memory processing unit greatly contributing to the improvement of the picture quality and possibility of a compact design of the apparatus.

When a large laser unit is used, the whole apparatus is unavoidably large as a matter of course while a large image receiver is required even when the laser unit is small because the image receiver must be of a super-high sensitivity. In addition, the use of a super-high sensitivity image receiver results in poor picture quality with decrease in the S/N ratio and resolution.

In the present invention, a small laser unit is used while the picture quality of the image can be greatly improved by replacing the super-high sensitivity image receiver with a combination of a control unit and an image memory processing unit so as to perform the synchronized accumulative addition or reduction of the images. In addition, a small image receiver of ordinary sensitivity is used and a laser oscillator, image receiver unit, image monitor and others are integrated so that the apparatus as a whole can be compactly constructed with improved mobility and improved operability.

FIG. 1 is a perspective view illustrating the construction as a whole of the inventive apparatus according to an example.

The apparatus for the detection of fingerprints according to this example is composed of a detector head 20, a power source unit for the laser 22 and an image memory processing unit 24. The cable 12 connects these units and the arrow 14 indicates the output of the video signals.

The detector head 20 is composed of a laser beam projector 26, image receiver unit 28, picture monitor 30 and control circuit unit 32.

Although the control circuit unit 32 in this example is built in the detector head 20, such a built-in control circuit unit is not essential and the electronic circuit per se as the principal part of the control circuit unit 32 can be integrated while the image memory processing unit 24 or other parts with the operating switches alone are built in the detector head 20 without affecting the advantageous effect of the invention.

The laser beam projector 26 includes the laser oscillator 34 and the optical system 36 and the optical system 36 is composed, as the basic construction, of a lens 42 which serves to conically expand or to cause conical divergence of the laser beam and a reflector mirror or a prism 44 which serves to deflect and direct the laser beam to a desired direction. The image receiver unit 28 is composed of a two-dimensional image receiver 38 and a sharp-cut filter 40 which is opaque to the laser beam and light having a wavelength equal to or shorter than that of the laser beam.

The control circuit unit 32 serves to control the image receiver unit 28, laser oscillator 34, power source unit of the laser 22 and image memory processing unit 24 in a synchronized operation so that the fluorescent image coming from the sample bearing the fingerprint and irradiated with the laser beam is received in the image receiver unit 28 and the signals of the image are stored, accumulated and processed in the image memory processing unit 24.

In the following, a detailed description is given of an apparatus according to the invention comprising a YAG laser as the laser oscillator 34 and power source unit for the laser 22, a TV camera (Newvicon) as the two-dimensional image receiver 38 and a frame memory capable of adding the images as the image memory processing unit 24.

The particulars of the YAG laser include: 532 nm of the second harmonics as the oscillated wavelength; 30 mJ/pulse of the output; and 20 pulses/second as the maximum number of repeated oscillation.

Figure 2:
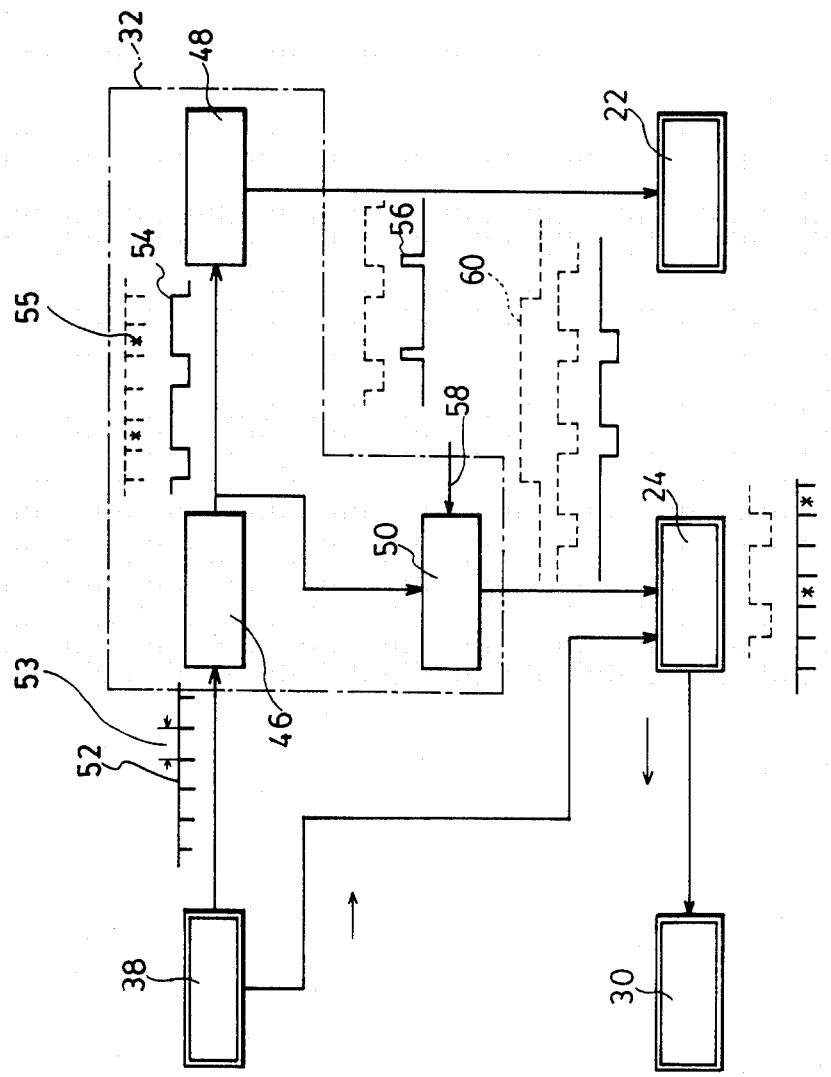
FIG. 2 illustrates the flow diagram of the control signals in the apparatus shown in FIG. 1.

The flow diagram of the signals is shown in FIG. 2. The control circuit unit 32 is composed of a timing pulse generator 46, laser trigger pulse generator 48 and gate circuit 50. The vertical synchronizing signals of 60 Hz as the output of the TV camera 38, i.e. two-dimensional image receiver, are converted in the timing pulse generator 46 into a square wave of 20 Hz, which is transmitted into the laser trigger pulse generator 48 and the gate circuit 50. A single interval 53 of the vertical synchronizing signals 52 corresponds to a frame of the image. The asterisk 55 given by the square wave 54 of 20 Hz indicates a frame-memory write-in frame.

The laser trigger pulse generator 48 generates a pulse 56 with a time lag of about 100 micro-seconds from the moment of rising of the square wave by utilizing the square wave signals 54 of 20 Hz as the trigger so as to operate the power source unit of the laser 22 to emit the laser beam.

The square wave 54 transmitted to the gate circuit 50 passes through the gate circuit 50 for the interval alone of the gate time of the manual input signal 60 manually inputted to the gate circuit 50 from outside through the input gate 58 to be inputted into the image memory processing, i.e. frame memory, unit 24. The image memory processing unit 24 stores the video signal for 1/60 second coming next to the input square wave (negative logic) and the successively inputted data for 1/60 second corresponding to a frame are addition-processed or accumulated.

Namely, the laser beam is emitted in synchronization with the starting point of each frame by the image signals inputted to the image memory processing, i.e. frame memory, unit 24 so that a complete image is obtained without loss of quantity of light. Futhermore, weak signals can be intensified to greatly improve the S/N ratio by the addition processing of a plurality of image frames.

To say particularly, n times of addition has an effect of improving the S/N ratio by a factor of square root of n for random noises. It is also possible to eliminate the disturbing effect of outer light by performing a reduction processing with the laser beam interrupted after the addition processing.

The video image signals from the two-dimensional image receiver 38 are transmitted also to the image memory processing unit 24 and the memory image of the image memory processing unit 24 can be monitored in the image monitor 30.

Conventional instruments for the detection of fingerprints have a problem in handling since the weight thereof is usually about 50 kg as a total of the units. On the contrary, the detecting head according to the invention has a greatly reduced weight of only 10 kg or somewhat larger as an integration of the light projector unit, image receiving unit, image monitor, control circuit unit and the like with greatly increased mobility and operability so that fingerprints can be detected by use of the inventive apparatus as simply and conveniently as in the use of a commercially available TV camera.

In addition, the control circuit unit serves to synchronize the operation of the laser oscillator unit, power source unit of the laser, image memory processing unit and image receiving unit so that the result of the fingerprint detection is obtained with a high picture quality. Accordingly, the apparatus for the fingerprint detection manufactured on the base of the above described results has excellent durability and is advantageous in the manufacturing cost.

Figure 3:
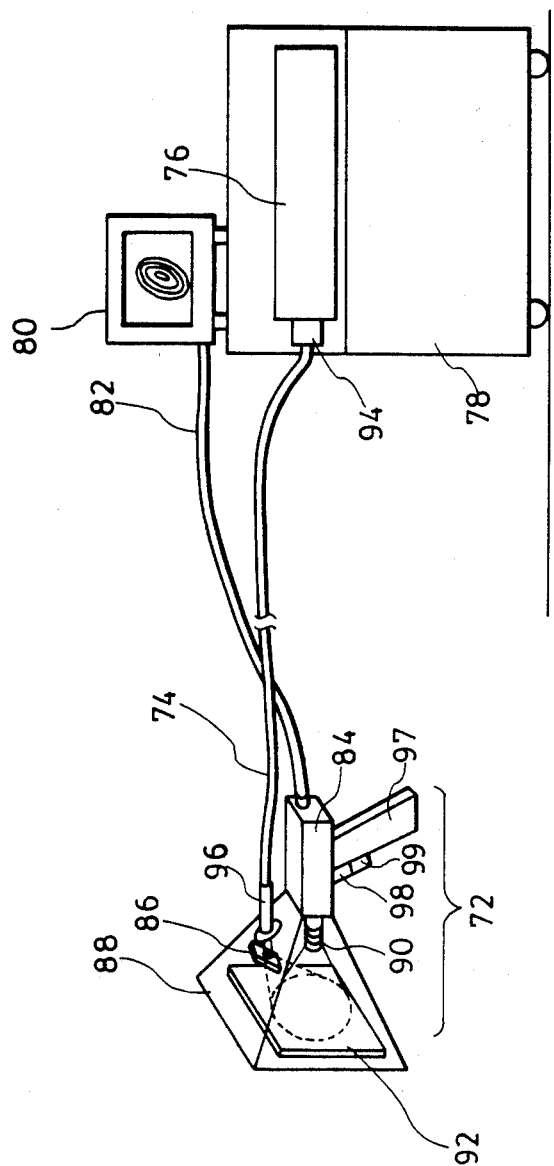
FIG. 3 is an illustration of the construction of the second example according to the invention.

In the next place, FIG. 3 illustrates a compact apparatus for the detection of fingerprints according to the second example of the present invention, of which the operability of the instrument is further improved and scattering of the light by diffused reflection on the sample is prevented. The characteristic features of this apparatus are as follows.

(1) The laser unit can be a YAG laser, argon ion laser, $N_2$ laser and the like and an optical fiber is provided for the conduction of the irradiating light from the oscillator unit to a sample located at a distance.

(2) The laser beam can be aligned or brought into divergence by means of a collimator and lens which are in an integral structure with the optical fiber.

(3) The instrument has a two-dimensional picture pickup unit equipped with a mirror or prism for deflecting the conducted and expanded laser beam to a desired direction, a sharp-cut filter and a hood.

(4) The image receiving unit has a inlet opening for the optical fiber and they can be used in combination.

The inventive apparatus is formed by portably integrating the laser irradiation unit and the image pickup unit to have excellent operability and mobility and can be operated by a single operator including all of the procedures such as adjustment and image pickup.

The apparatus is composed of an image receiving unit 72, optical fiber 74, laser oscillator 76, power source unit for the laser 78, picture monitoring unit 80 and signal cable 82.

The image receiving unit 72 is composed of a two-dimensional image pickup unit, reflecting mirror 86 for reflecting the expanded beam conducted by the optical fiber, hood 86 made of a material which is opaque to light having a wavelength equal to or smaller than that of the laser beam and filter 90 and equipped with a handle 97, switch 98 and mechanism for remote control of focusing 99.

The image receiving unit 72 as a whole is integrally constructed so that the procedure of the detection of fingerprints can be performed easily by irradiating the sample 92 with the laser beam and picking-up the fluorescent image.

Furthermore, a collimator is mounted on the connecting part between the laser oscillator 76 and the optical fiber 74 and the optical fiber 74 is combined at the end thereof in an integral structure with an optical system 96 comprising a collimator and lens to align or expand the conducted light beam.

In the following, an example of the inventive apparatus is described in which a YAG laser is used as the laser unit with the second harmonic having a wavelength of 532 nm for the laser oscillation.

The switch 98 for the laser oscillation is mounted on the handle 97 of the two-dimensional image pickup unit so that the laser oscillation can be turned on and off by switching at the image receiving unit. The projected laser beam is expanded and reflected to irradiate the sample 92 and the fluorescent image therefrom is picked up by the two-dimensional dimensional image pickup unit 84 to be displayed on the picture monitoring unit 80. The control of focusing can be performed automatically with a possibility of further increased easiness thereof by adding a mechanism 99 for remote control of focusing.

The optical system is demountable as a unit from the hood so that direct visual inspection of the fingerprint image can be performed by providing a goggle with filter in place of the optical system.

When a pulse laser is used as the oscillator as in this example, difficulties are sometimes felt in watching the image like a blinker on the picture monitor. This problem can be solved by adding a unit for signal processing or image processing which serves to synchronize the laser oscillation and picking-up of the images or to display overlapped images.

In the example illustrated in FIG. 3, irradiation with the laser beam and detection of the fluorescent image can be both performed in a compactly integrated image receiving unit with excellent mobility so that the works of fingerprint detection can be performed easily. By virtue of the hood intercepting the laser beam, in addition, the operator and observers therearound can inspect the fluorescent image from the fingerprint alone with safety without seeing the scattered light coming from the sample.

When a latent fingerprint is to be detected by the laser-induced fluorescence method, the improvement for obtaining a clearer and more distinct fingerprint image by the laser beam irradiation comprises the steps of: expanding the laser beam emitted by the laser oscillator using a lens system; intermittently scanning the thus expanded laser beam in a desired direction according to the intensity distribution of the laser beam; writing the detected image in the image memory with the scanning interrupted, the writing-in being performed at several positions of the interrupted scanning; and integrating these data of several image frames.

The diameter of the laser beam directly emitted from the oscillator is about 4 to 5 mm at the largest so that the laser beam emitted from the oscillator is expanded to have a diameter of 50 to 60 mm by means of the lens system because several problems are involved in the direct irradiation with the laser beam that the fingerprint image cannot be visually inspected, that no satisfactory fingerprint image can be obtained due to the too high intensity of light, that a very complicated structure is necessary for the scanning of the beam due to the requirements for high-speed scanning and high-speed image pickup, and so on.

The expanded laser beam is brought into scanning in the vertical or transverse direction in such a manner that the moving beam can be stopped at a predetermined pitch. In this manner, an indistinct image can be recognized as a plural number of clear and distinct picture frames.

The images are integrated so as to improve the indistinct image of the detected fingerprint and to give a satisfactory image by writing a predetermined number of the picture frames from the image pickup device at the position of the interruption and by integrating the written-in memory at each position of interruption.

Figure 4:
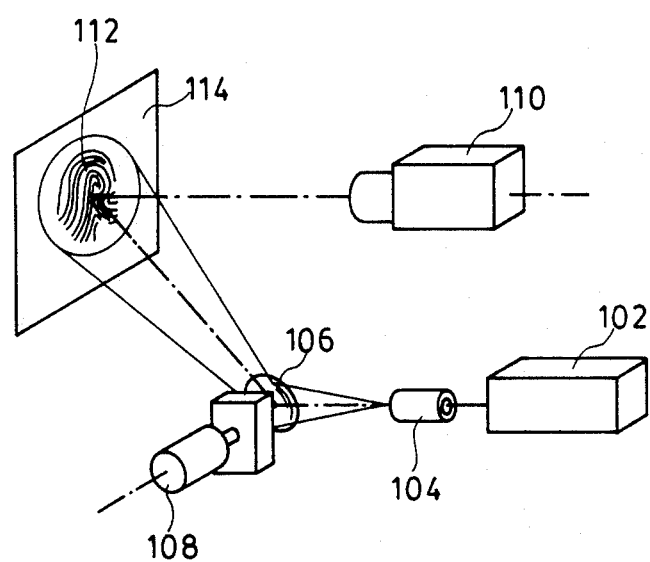
FIG. 4 illustrates a construction diagram of the third example according to the invention.

FIG. 4 illustrates a block diagram of the unit instruments in this example. As is shown in this figure, the laser beam emitted from the laser oscillator 102 is expanded in the beam-expanding lens system 104 and reflected by the reflecting mirror 106 to irradiate the sample 114 bearing a latent fingerprint 112 deposited thereon. The mirror-driving mechanism 108 serves to scan the beam in the vertical direction and the image pickup unit 110 picks up the thus scanned image in this example shown in FIG. 4, a single mirror-driving mechanism 108 is provided to scan the beam only in the vertical direction but it is optional when scanning of the beam also in the transverse direction is desired that two similar scanning mechanisms are provided so as to scan the beam in the vertical and transverse direction.

The laser beam is emitted from the laser oscillator 102, expanded in the beam-expanding lens system 104 and reflected by the reflecting mirror 106. The reflecting mirror 106 can be rotated and stopped at any desired position by means of the driving mechanism 108. Suitable mirror-driving mechanism includes, for example, a pulse motor, galvanometer and the like.

The moving pitch of the reflecting mirror should be about 5 mm depending on the size of the fingerprint which may be 20 mm by 15 mm wide. In this example, accordingly, the beam is scanned over a range of 35 mm with 7 positions of interruption.

The laser beam upwardly reflected by the reflecting mirror 106 irradiates the sample covering an area of about 50 to 60 mm diameter to cause fluorescence of the whole fingerprint.

The fluorescent image of the fingerprint 112 is picked up by the image pickup device 110 and detected as image signals.

Figure 5:
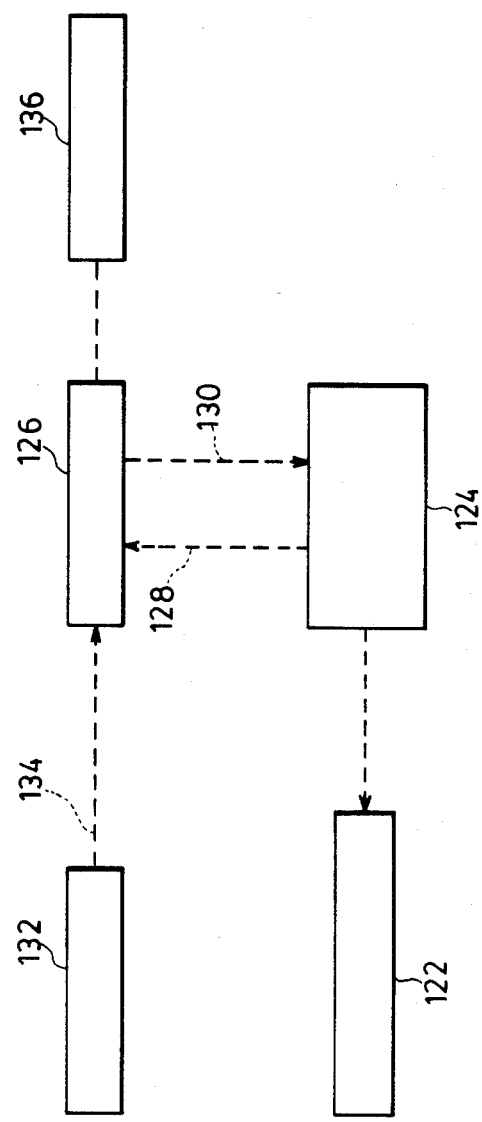
FIG. 5 is a block diagram in the example shown in FIG. 4.

In the following, the working of the apparatus is explained with reference to the block diagram shown in FIG. 5.

The controller 124, at the stopping position of the driving mechanism 122, gives a stopping signal of the driving mechanism 122 and a starting order of writing 128 to the image integrator 126. At each of the stopping positions, the image integrator 126 receives a suitable number, for example 5, of the 5 to 10 image signals 134 from the image pickup device 132 to write in and successively integrate the same. When writing-in is completed, the image integrator 126 outputs a signal of completed writing 130 to the controller 124.

The image data accumulated in the image integrator 126 are then processed to increase the distinctness in the image processing unit 136. In this manner, a highly distinct good image of the fingerprint is obtained.

This processing has an effect to eliminate the light and shade in the picture image produced by the intensity distribution of light in the transverse section inherently possessed by a laser beam and to take out the light and shade image formed by the remaining fingerprint alone. Further, adjustment of the laser oscillator is no longer necessary for the optimization of the intensity distribution in the transverse section.

EXAMPLE 1

An example is described below using a 0.2% aqueous solution of rhodamine 6G as the dye solution. The procedure for the detection of a fingerprint included the following steps.

(1) The sample was dipped in the solution for about 10 seconds.

(2) The sample taken out of the solution was immediately rinsed with clean water for about 20 seconds.

(3) The sample was air-dried and irradiated with a beam of an argon ion laser having an irradiation intensity of 20 mW/cm$^2$ at a wavelength of 514 nm. The fluorescent image from the fingerprint-bearing area was taken with a camera with a filter attachment for removing the light of the argon ion laser.

Comparison was made of the results obtained in the above described method and the conventional method using a 0.2% methanol solution of rhodamine 6G for the detection of fingerprints on several modern building materials, such as a surface-finished plywood and the like, of which considerable difficulties are encountered in the detection of fingerprints by the powder method. The procedure in the conventional method using the methanol solution included the following steps.

(a) The sample was dipped in the methanol solution for about 2 minutes.

(b) The sample taken out of the solution was air-dried and subjected to the detection of the fluorescent image of the fingerprint under the identical conditions as in the case using the aqueous solution.

(c) When the background fluorescence was unduly strong, the sample is rinsed with methanol and the step (b) was repeated.

Table 1 below shows the results obtained in these comparative tests carried out in two ways. The fingerprint was impressed in about the same manner in all cases and the detection of the fingerprint was performed after about 36 hours from the impression. Table 1 gives the results of the (number of the samples on which finger prints could be detected)/(number of the tested samples).

TABLE 1

| Type of the sample | Printed plywood, 5 grades | Polyester finished plywood, 2 grades | Melamine finished plywood, 2 grades | Total |
|---|---|---|---|---|
| Inventive method | 9/10 (90%) | 10/10 (100%) | 9/10 (90%) | 28/30 (93%) |
| Comparative method | 4/10 (40%) | 10/10 (100%) | 7/10 (70%) | 21/30 (70%) |

As is shown in Table 1, fingerprints could be detected with a very high probability by the method of the present invention in comparison with the conventional method.

When a considerable amount of rhodamine is left on the sample processed in the above described procedure, great improvements may be obtained by finishing with rinse using a small volume of methanol.

EXAMPLE 2

Following is a description of an example using rhodamine 6G as the fluorescent dye.

Figure 6:
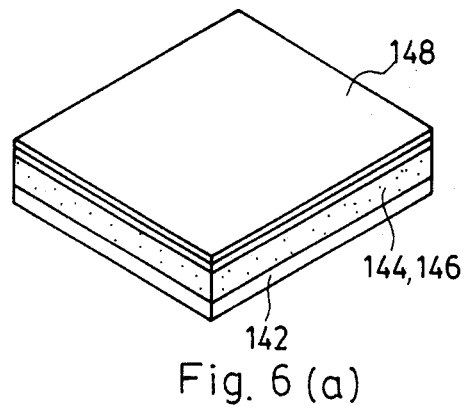
FIG. 6a and 6b are each a perspective view of the gelatin film(s) used in the examples of the present invention before use and during use, respectively.
Figure 6B:
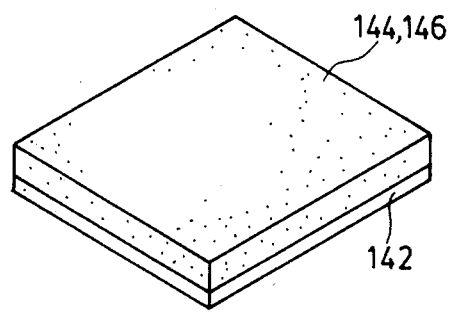

As is illustrated in FIG. 6(a), a gelatinous film 144 impregnated with the dye solution 146 was sandwiched between a substrate sheet of polyethylene 142 and a temporary protecting film of polyethylene 148 which was peeled off as is illustrated in FIG. 6(b) before the gelatinous film 144 was attached to the surface of a sample bearing a latent fingerprint. The gelatinous film had a thickness of about 0.5 mm and contained about 99% of a 0.2 % ethanol solution of rhodamine 6G. The gelatinous film was kept in contact with the sample surface for about 10 minutes and, after removing the gelatinous film, the sample surface was irradiated with a bam of an argon ion laser as the exciting light having an irradiation intensity of 0.1 W/cm$^2$ at a wavelength of 514 nm.

Quite satisfactory results could be obtained by the above described method in the detection of fingerprints impressed on a printed plywood.

EXAMPLE 3

Following is a description of an example of the invention using a yellow dye composition composed of 0.03% of sodium fluorescein, 99.8% of sodium sulfate and 0.20% of lanolin. The procedure for the detection of fingerprints included the following steps.

(1) The yellow dye composition was deposited on the surface of the sample.

(2) Water was sprayed immediately over the surface of the sample uniformly.

(3) Thereafter, the surface was irradiated with a beam of an argon ion laser having an irradiation intensity of 20 mW/cm$^2$ at a wavelength of 514 nm and the fluorescent image from the area including the fingerprint was taken with a camera having a filter attachment for removing the light of the argon ion laser.

The above described method of the invention was applied to specialty papers and cloths as the sample of which difficulties were encountered in the detection of fingerprints by the conventional methods such as the aluminum powder method, ninhydrin method and the like to give the results shown in Table 2 below making comparison with the conventional method. The fingerprint was impressed in about the same manner in all cases and the detection of the fingerprints was performed after about 36 hours from the impression. Table 2 gives the results of (number of the samples on which fingerprints could be detected)/(number of the tested samples ).

TABLE 2

| Type of the sample | Thermosensitive paper | Cloth 2 grades | Total |
|---|---|---|---|
| Inventive method | 10/10 (100%) | 9/10 (90%) | 19/20 (95%) |
| Comparative method | 4/10 (40%) | 1/10 (10%) | 5/20 (25%) |

As is shown in Table 2, fingerprints could be detected with a very high probability by the method of the present invention in comparison with the conventional method.

The above described method of the invention provides a possibility of detecting a fingerprint with a very high probability even on certain samples such as specialty papers and cloths of which difficulties are encountered in most cases in the fingerprint detection performed after lapse of a considerable length of time by the powder method and the like in the prior art.

Meanwhile, the finger prints in the above tests could hardly be detected by the aluminum powder method when the test was undertaken after two days or longer from the impression of the fingerprint.

What is claimed is:

1. A method for the detection of a latent fingerprint on a sample by the deposition of a fluorescent dye or a chemical reagent capable of producing a fluorescent substance by the reaction with the ingredients in the fingerprint secretion on to a surface area of a sample including a latent fingerprint and irradiation of the surface area with light to cause emission of fluorescence from the fluorescent dye or fluorescent substance exhibiting an image of the fingerprint lines which comprises the steps of:

(a) bringing a gelatin film impregnated with a solution of the fluorescent dye or the chemical reagent into direct contact with the surface area of the sample including the latent fingerprint so as to have the solution adhere to the surface area;

(b) peeling the gelatin film off the surface of the sample; and (c) irradiating the surface area of the sample with light having a wavelength capable of exciting the fluorescent dye or the fluorescent substance to emit fluorescence giving a fluorescent image of the fingerprint lines.

* * * * *